(12) United States Patent
Onishi et al.

(10) Patent No.: US 6,500,985 B2
(45) Date of Patent: Dec. 31, 2002

(54) PROCESS FOR PRODUCING ALPHA-AMINOKETONES

(75) Inventors: Tomoyuki Onishi, Kawasaki (JP); Takashi Nakano, Kawasaki (JP); Naoko Hirose, Kawasaki (JP); Masakazu Nakazawa, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/911,793

(22) Filed: Jul. 25, 2001

(65) Prior Publication Data

US 2002/0013499 A1 Jan. 31, 2002

Related U.S. Application Data

(63) Continuation-in-part of application No. PCT/JP00/00480, filed on Jan. 28, 2000.

(30) Foreign Application Priority Data

Jan. 28, 1999 (JP) .......................... 11-020504
Mar. 4, 1999 (JP) .......................... 11-057618

(51) Int. Cl.[7] ............... C07C 251/08; C07C 251/16; C07C 209/62
(52) U.S. Cl. ............. 564/269; 564/271; 564/272; 564/275; 564/278; 564/415; 564/468; 564/489
(58) Field of Search .................... 564/269, 271, 564/272, 275, 278, 415, 468, 489

(56) References Cited

U.S. PATENT DOCUMENTS 4,638,080 A  * 1/1987  Raizon et al. ............. 560/35
5,481,011 A    1/1996  Chen et al. ............... 549/514

FOREIGN PATENT DOCUMENTS

JP   WO 00/44706    8/2000
WO   WO 98/45271   10/1998

OTHER PUBLICATIONS

Greene, Theodora W., et al, "Protective Groups in Organic Synthesis", Second Edition, John Wiley & Sons, Inc., 1991, pp. 368–371.

* cited by examiner

Primary Examiner—Brian J. Davis
(74) Attorney, Agent, or Firm—Oblon, Spivak, McClelland, Maier & Neustadt, P.C.

(57) ABSTRACT

An amino group of an α-amino acid ester is protected as an imine, and it is then reacted with a halomethyllithium to obtain an N-protected-α-aminohalomethylketone. Further, this N-protected-α-aminohalomethylketone is treated with an acid to obtain an α-aminohalomethylketone. This process is suited for industrial production, and can produce an α-aminohalomethylketone and its related compounds economically and efficiently.

12 Claims, No Drawings

PROCESS FOR PRODUCING ALPHA-AMINOKETONES

This application is a Continuation-in-part (CIP) of international PCT appication No. PCT/JP00/00480, filed Jan. 28, 2000, pending.

BACKGROUND OF THE INVENTION

The present invention relates to a process for producing an α-aminohalomethylketone from an N-protected α-amino acid ester with an amino group protected as an imine via a novel N-protected-α-aminohalomethylketone.

Further, the invention relates to a process for producing an N-protected-α-aminohalomethylketone, a β-aminoalcohol, an N-protected-β-aminoalcohol or an N-protected-β-aminoepoxide derived from the α-aminohalomethylketone.

Still further, the invention relates to an N-carbamate-protected-α-aminohalomethylketone, an N-carbamate-protected-β-aminoalcohol or an N-carbamate-protected-β-aminoepoxide derived from the α-aminohalomethylketone.

An α-aminohalomethylketone (compound of formula (3) to be described later) and its salt can be converted into peptidylhalomethylketones by the method which is ordinarily used in the peptide synthesis, and they are compounds useful as intermediates for synthesis of various peptidylhalomethylketones which are known as serine protease inhibitors (refer to, for example, W. Brandt et al., Int. J. Peptide Protein Res. 1995, 46, 73).

In addition, they are reported to be useful as intermediates for synthesis of HIV protease inhibitors (refer to, for example, J. Med. Chem. 1990, 33, 1285).

Furthermore, an N-protected-α-aminohalomethylketone (compound of formula (7) or (10) to be described later), a β-aminoalcohol (compound of formula (13) to be described later) and an N-protected-β-aminoalcohol (compound of formula (8), (11) or (14) to be described later) and an N-protected-β-aminoepoxide (compound of formula (9), (12) or (15) to be described later) derived therefrom are likewise known to be important compounds as medical intermediates of HIV protease inhibitors.

An α-aminohalomethylketone has been so far produced by deprotecting an N-protected-α-aminohalomethylketone (refer to, for example, S. Fittkau et al., J. Prakt. Chem. 1986, 529).

As a method for producing N-protected-α-aminohalomethylketones, for example, a method has been known in which N-protected α-amino acid ester is reacted with a metallic enolate formed from an α-haloacetic acid and decarboxylation is conducted (refer to WO 96/23756).

In this method, however, as described in Examples of WO 96/23756, a costly Grignard reagent or an organolithium reagent has to be used in an amount of more than approximately 4 equivalents based on N-protected amino acid ester.

A method is also known in which production is conducted such that an alanine ester having an amino group protected with a dibenzyl group is reacted with a halomethyllithium (refer to J. Barluengaetal., J. Chem. Soc., Chem. Commun. 1994, 969).

In this method, however, groups other than a dibenzyl group are not studied as a protecting group of the amino group, and a method in which elimination of the dibenzyl group is conducted while maintaining a halogenated ketone moiety is unknown. Thus, the method cannot be used as a method for producing an α-aminohalomethylketone.

A method is also known in which production is conducted such that a carbamate site of an amino acid ester having an amino group protected with a carbamate group is further protected with a trialkylsilyl group, and then reacted with a halomethyllithium (refer to Japanese Patent Laid-Open Nos. 99,947/1996 and 99,959/1996).

Nevertheless, in this method also, as described in Examples of Japanese Patent Laid-Open Nos. 99,947/1996 and 99,959/1996, a costly organolithium reagent has to be used in an amount of approximately 2.2 equivalents based on N-protected amino acid ester. Further, the protecting group of the amino group used in Examples thereof is only a methoxycarbonyl group. However, a method in which elimination of the methoxycarbonyl group is conducted while maintaining a halogenated ketone moiety is unknown. Thus, it is unclear whether the method can be used in the production of an α-aminohalomethylketone.

DISCLOSURE OF THE INVENTION

The invention aims to provide a process for producing an α-aminohalomethylketone and its related compounds which is suited for industrial production, economical and efficient.

The present inventors have assiduously conducted investigations to solve the problems, and have consequently found that a novel N-protected-α-aminohalomethylketone is obtained in high yield by protecting an amino group of an α-amino acid ester as an imine (Schiff base) and then reacting it with a halomethyllithium.

Further, it has been found that this N-protected-α-aminohalomethylketone is easily deprotected through the treatment with an acid to form an α-aminohalomethylketone.

This α-aminohalomethylketone can be converted into an N-protected-β-aminoepoxide via an N-protected-α-aminohalomethylketone and an N-protected-β-aminoalcohol.

Moreover, the inventors have found a process for producing an N-protected-β-aminoepoxide from an α-aminohalomethylketone via a β-aminoalcohol and an N-protected-β-aminoalcohol.

Besides, the inventors have found a method in which an amino group of an α-aminohalomethylketone is protected with a carbamate group (especially a tert-butoxycarbonyl group).

The inventors have completed the invention based on these findings.

That is, the invention provides a process for producing an α-aminohalomethylketone represented by formula (3)

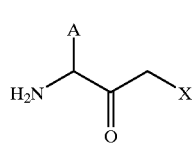

(3)

wherein

A represents an optionally substituted alkyl group having 1 to 10 carbon atoms, an optionally substituted aryl group having 6 to 15 carbon atoms, an optionally substituted aralkyl group having 7 to 20 carbon atoms, or a group in which heteroatom is contained in these carbon skeletons, and X represents a halogen atom or its salt, which comprises reacting an N-protected-α-amino acid ester represented by formula (1)

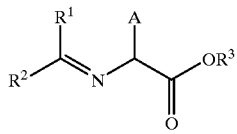

(1)

wherein $R^1$ and $R^2$, independently from each other, represent an optionally substituted aryl group or lower alkyl group, or a hydrogen atom, $R^3$ represents an optionally substituted lower alkyl group, aralkyl group or aryl group, and A is as defined above, provided $R^1$ and $R^2$ may together form a ring structure with a halomethyllithium, and then treating this with an acid.

BEST MODE FOR CARRYING OUT THE INVENTION

The invention is described in detail below.

In the formula in the invention, $R^1$ and $R^2$, independently from each other, represent an optionally substituted aryl group or lower alkyl group, or a hydrogen atom. $R^1$ and $R^2$ may together form a ring structure directly or through an appropriate group. The substituent in the optionally substituted group is not particularly limited so long as it does not have an adverse effect on the reaction of the invention in particular. Examples thereof can include an alkoxy group (preferably having 1 to 6 carbon atoms), a nitro group, an alkyl group (preferably having 1 to 6 carbon atoms) and a halogen atom.

An aryl group is preferably an optionally substituted phenyl group, especially preferably a phenyl group, a p-methoxyphenyl group or a p-isopropylphenyl group. A lower alkyl group includes a linear or branched saturated alkyl group having 1 to 4 carbon atoms.

When the ring structure is formed, examples of formulas (16) and (17) can be listed.

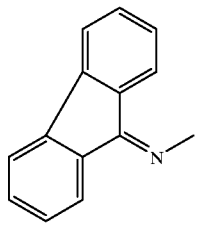

(16)

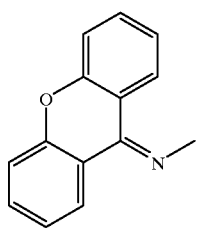

(17)

These formulas include a protecting group moiety formed from $R^1$ and $R^2$ and an imine structure.

It is preferable that both of $R^1$ and $R^2$ are optionally substituted aryl groups, or that one thereof is an optionally substituted aryl group and the other is a hydrogen atom.

In the formula in the invention, $R^3$ is (i) an optionally substituted lower alkyl group or aralkyl group, or (ii) an optionally substituted aryl group. Examples thereof can include an optionally substituted linear or branched saturated alkyl group having 1 to 8 carbon atoms, an optionally substituted aralkyl group having 7 to 15 carbon atoms, and an optionally substituted aryl group having 6 to 14 carbon atoms. Especially, a linear or branched saturated alkyl group having 1 to 3 carbon atoms, such as a methyl, ethyl, propyl or isopropyl group, or an optionally substituted benzyl group is preferable. The substituent in the optionally substituted group is not particularly limited so long as it does not have an adverse effect on the reaction of the invention in particular. Examples thereof can include an alkoxy group (preferably having 1 to 7 carbon atoms), a nitro group, an alkyl group (preferably having 1 to 6 carbon atoms) and a halogen atom.

In the formula in the invention, A represents a hydrogen atom, an optionally substituted alkyl group having 1 to 10 carbon atoms, an optionally substituted aryl group having 6 to 15 carbon atoms, an optionally substituted aralkyl group having 7 to 20 carbon atoms, or a group in which heteroatom is contained in these carbon skeletons. The substituent in the optionally substituted group is not particularly limited so long as it does not have an adverse effect on the reaction of the invention in particular. Examples thereof can include an alkoxy group (preferably having 1 to 6 carbon atoms), a nitro group, an alkyl group (preferably having 1 to 6 carbon atoms) and a halogen atom.

Examples of the group in which the heteroatom (for example, nitrogen, oxygen or sulfur atom) is contained in the carbon skeletons include methylthioethyl, tert-butylthiomethyl, tritylthiomethyl (p-methylbenzyl)thiomethyl, (p-methoxybenzyl)thiomethyl, tert-butoxymethyl, benzyloxymethyl, tert-butoxyethyl, benzyloxyethyl, 4-(tert-butoxy)phenylmethyl, 4-benzyloxyphenylmethyl and phenylthiomethyl groups.

This group can be introduced using, for example, an amino acid as a starting material. For example, it can be introduced using, as a starting material, glycine when A is a hydrogen atom, alanine when A is a methyl group, valine when A is an isopropyl group, leucine when A is a 2-methylpropyl group, isoleucine when A is a 1-methylpropyl group, phenylalanine when A is a benzyl group, or methionine when A is a methylthioethyl group.

A may be a group introduced by using, as a starting material, an amino acid with a functional group of an amino acid side chain protected, examples thereof being S-tert-butylcysteine, S-tritylcysteine, S-(p-methylbenzyl)cysteine, S-(p-methoxybenzyl)cysteine, O-tert-butylserine, O-benzylserine, O-tert-butylthreonine, O-benzylthreonine, O-tert-butyltyrosine and O-benzyltyrosine.

A is not limited to a group introduced from a starting material derived from a natural amino acid, and it may be a group introduced from a starting material derived from an artificial amino acid (for example, a phenyl group or a phenylthiomethyl group).

A is preferably a benzyl group or a phenylthiomethyl group.

In the formula in the invention, X represents a halogen atom. Examples of the halogen atom include fluorine, chlorine, bromine and iodine atoms. A chlorine or bromine atom is preferable, and a chlorine atom is especially preferable.

In the formula in the invention, $B^1$ and $B^3$, independently from each other, represent a protecting group of an amino group. The protecting group of the amino group is not particularly limited. For example, protecting groups described in Protecting Groups in Organic Chemistry, 2nd edition, John Wiley & Sons, Inc. 1991 can be used. Of these, a carbamate-type protecting group ($B^2$ in the invention) is used especially preferably because it is easily removed. Examples of the carbamate-type protecting group include methoxycarbonyl, ethoxycarbonyl, tert-butoxycarbonyl, benzyloxycarbonyl, fluorenylmethoxycarbonyl and tetrahydrofuran-3-yloxycarbonyl groups.

These protecting groups are not necessarily eliminated, and they are sometimes used without being eliminated according to the subsequent step or the desired compound. Examples thereof include a tetrahydrofuran-3-yloxycarbonyl group (refer to EP 774453) and a 3-protected-hydroxy-2-methylbenzoyl group.

The N-protected-α-amino acid ester represented by formula (1), which is used as a starting material in the invention, can easily be produced, as schematically shown below, by a known method from an α-amino acid ester represented by formula (4) or its salt and an imine compound represented by formula (5) or an aldehyde or ketone compound represented by formula (6).

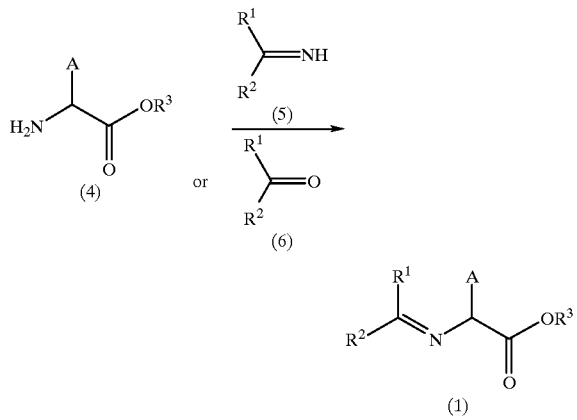

wherein $R^1$, $R^2$, $R^3$ and A are as defined above.

When the amino acid ester and the aldehyde compound are reacted, these can be reacted in the presence of a dehydrating agent such as anhydrous sodium sulfate, anhydrous magnesium sulfate, calcium chloride or a molecular sieve or an acid (refer to, for example, A. Dondoni et al., Synthesis 1993, 1162). Examples of the solvent at this time can include aprotic solvents such as dichloromethane, chloroform, tetrahydrofuran, ether, tert-butylmethyl ether, toluene, ethyl acetate and isopropyl acetate. When the amino acid ester salt is used as a starting material, it may be used in the reaction by neutralization with the addition of 1 equivalent of a base to the reaction system. Also when the amino acid ester and the ketone compound are reacted, the reaction can be conducted by the same method as in the aldehyde compound (refer to, for example, M. J. O'Donnell et al., Tetrahedron Lett. 1978, 30, 2641).

When the amino acid ester and the imine compound are reacted, the amino acid ester salt and the imine compound can be reacted using the same reaction solvent as mentioned above (refer to, for example, M. J. O'Donnell et al., J. Org. Chem. 1982, 47, 2663).

Preferable examples of the imine compound represented by formula (5) can include benzophenonimine and 9-fluorenonimine. Preferable examples of the aldehyde or ketone compound represented by formula (6) can include benzaldehyde, anisaldehyde, cuminaldehyde and p-nitrobenzaldehyde. Such compounds can be procured industrially at low costs.

The process of the invention can be applied to the synthesis of optically active compounds using optically active α-amino acid esters obtained by esterifying optically active amino acids. The optically active amino acids are important in the medical use. That is, as the α-amino acid esters, optically active compounds (L-isomers or D-isomers) are preferably used. Especially, optically active phenylalanine esters and optically active phenylthioalanine esters are important as starting materials of HIV protease inhibitors.

Next, a process for producing an N-protected-α-aminohalomethylketone represented by formula (2) by reacting the N-protected-α-amino acid ester represented by formula (1) with a halomethyllithium is described.

wherein $R^1$, $R^2$, A and X are as defined above.

The halomethyllithium in the invention can be represented by formula (19).

wherein X is as defined above.

Such a halomethyllithium can be formed by the reaction of an organolithium compound such as methyllithium, n-butyllithium or sec-butyllithium with a dihalomethane such as bromochloromethane, chloroiodomethane or dibromomethane (refer to, for example, Encyclopedia of Reagents for Organic Synthesis, John Wiley & Sons, Inc. 1995). A halomethylketone can be obtained by reacting the thus-formed halomethyllithium with an ester (refer to, for example, R. Tarhouni et al., Tetrahedron Lett. 1984, 25, 835, and J. Barluenga et al., J. Chem. Soc., Chem. Commun. 1994, 969). In the invention also, it is advisable that the organolithium compound and the dihalomethane are added to a reaction solvent and the halomethyllithium is formed in the reaction system.

Preferable examples of the halomethyllithium include chloromethyllithium and bromomethyllithium, and chloromethyllithium is especially preferable. When α-aminochloromethylketone (X is a chlorine atom in formula (3)) is produced, chloromethyllithium is formed. When α-aminobromomethylketone (X is a bromine atom in formula (3)) is produced, bromomethyllithium is formed.

Since it is known that the halomethyllithium is thermally unstable, it is preferable that when the halomethyllithium and the ester are reacted, the ester and the dihalomethane are previously dissolved in a solvent and the organolithium compound is then added. Further, at this time, a salt such as lithium chloride or lithium bromide may be present.

The organolithium compound used in the invention can be represented by, for example, formula (18).

wherein $R^4$ represents a lower alkyl group, or an aryl group.

The lower alkyl group can include a linear or branched saturated alkyl group having 1 to 8 carbon atoms. Examples of the aryl group can include a phenyl group and a naphthyl group. A lower alkyllithium in which $R^4$ is a lower alkyl group is preferable. It is especially preferable that $R^4$ is a linear saturated alkyl group having 1 to 6 carbon atoms, such as a methyl, ethyl, n-butyl or n-hexyl group.

Preferable examples of the dihalomethane used in the invention include bromochloromethane, chloroiodomethane and dibromomethane, and bromochloromethane and chloroiodomethane are especially preferable. When an α-aminochloromethylketone (X is a chlorine atom in formula (3)) is produced (when chloromethyllithium is formed), bromochloromethane and chloroiodomethane are used. When α-aminobromomethylketone (X is a bromine atom in formula (3)) is produced (when bromomethyllithium is formed), dibromomethane is used.

The amounts of the organolithium compound and the dihalomethane are not particularly limited. It is advisable that each of them may be used in an amount of 1 to 2 equivalents based on the N-protected-α-amino acid ester derivatives. Of course, more than 2 equivalents may be used. However, these reagents are costly. In the invention, it is preferably between 1 and 1.5 equivalents, more preferably between 1.2 and 1.4 equivalents.

As the reaction solvent, ether-type solvents such as tetrahydrofuran, diethyl ether and tert-butylmethyl ether are preferable. Further, mixed solvents of these solvents and nonpolar solvents such as toluene and hexane are also preferable. The reaction proceeds quickly at a temperature of −120° C. to 0° C. The reaction is conducted preferably in the range of −80° C. to −50° C. Usually, the reaction is completed in 5 to 60 minutes. After the completion of the reaction, it is advisable that the reaction solution is treated with an ammonium chloride aqueous solution, a phosphate buffer solution or water. Further, when the reaction solution is treated with an acid, a hydrolysis reaction of an imine (Schiff base) in the subsequent step can directly be conducted.

The resulting N-protected-α-aminohalomethylketone (2) can be used through purification by a method known to those skilled in the art, such as column chromatography or crystallization. However, as stated earlier, it may be used in the subsequent reaction without purification by separation.

A process for producing an α-aminohalomethylketone represented by formula (3) by treating the N-protected-α-aminohalomethylketone represented by formula (2) with an acid is described below.

The imine (Schiff base) moiety of the N-protected-α-aminohalomethylketone represented by formula (2) can easily be hydrolyzed with an acid.

The acid used is not particularly limited. Examples thereof can include inorganic acids such as hydrochloric acid, hydrobromic acid, hydroiodic acid, sulfuric acid and phosphoric acid, and organic acids such as trifluoroacetic acid, methanesulfonic acid, benzenesulfonic acid and p-toluenesulfonic acid.

The solvent is not particularly limited. Examples thereof include water, methanol, ethanol, tetrahydrofuran, dioxane, ethyl acetate, isopropyl acetate, dichloromethane, chloroform, toluene, hexane, and mixed solvents of these.

After water is added to the reaction solution, an aldehyde or a ketone as a by-product of hydrolysis can be removed to an organic layer by washing an aqueous layer with an appropriate organic solvent such as ethyl acetate, isopropyl acetate, dichloromethane, chloroform or toluene. The resulting aqueous layer is concentrated, an insoluble matter is filtered off with the addition of an alcohol, and crystallization (for example, crystallization by cooling or crystallization by concentration) is conducted from an alcohol or a mixed solvent of an alcohol and another solvent under appropriate conditions, whereby an α-aminohalomethylketone can be obtained as a salt. Preferable examples of the alcohol include methanol, ethanol and 2-propanol. Examples of the solvent used in combination with the alcohol include ethyl acetate, isopropyl acetate, dichloromethane, ether, tert-butylmethyl ether, tetrahydrofuran, 1,4-dioxane, benzene, toluene and water.

Various α-aminohalomethylketone salts are prepared according to acids used. These salts can be used as such in the subsequent reaction in the invention. Free compounds can be formed by reacting the salts with an equivalent amount of a base. However, the free compounds are unstable compared with the salts. Thus, it is preferable that the salts are used in the form of acid salts as such.

When an alkoxycarbonylation reaction (for example, methoxycarbonylation, ethoxycarbonylation, tert-butoxycarbonylation or benzyloxycarbonylation) of the α-aminohalomethylketone or a reduction reaction of a carbonyl group is conducted in the subsequent step, the aqueous layer can be used in the reaction in the next step directly or as required, by distilling off the solvent without conducting crystallization or purification by separation.

A process for producing an N-protected-α-aminohalomethylketone represented by formula (7) by protecting the amino group of the α-aminohalomethylketone represented by formula (3) with the protecting group is described below.

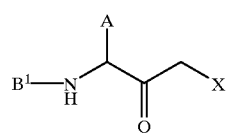

(7)

wherein A, X and $B^1$ are as defined above.

The α-aminohalomethylketone is stable under acidic conditions but unstable under basic conditions. Therefore, it is undesirable that the reaction is conducted under basic conditions which are ordinarily applied to the protection reaction of the amino group in the peptide synthesis.

That is, an amino group protecting reagent such as an alkoxycarbonylation reagent, an acylation reagent or a sulfonylation reagent has to act in the presence of a base. At this time, decomposition of the α-aminohalomethylketone in not a small amount proceeds to invite the decrease in the reaction yield. Accordingly, to protect the same in good yield, it is advisable to conduct the protection by either of the two procedures mentioned below.

Procedure 1: The amino group protecting reagent such as an alkoxycarbonylation reagent, an acylation reagent or a sulfonylation reagent and a base are mixed in an appropriate solvent, and a solution of an α-aminohalomethylketone acid salt is then added thereto.

Procedure 2: A solution of the amino group protecting reagent such as an alkoxycarbonylation reagent, an acylation reagent or a sulfonylation reagent and a solution of an α-aminohalomethylketone acid salt are mixed, and a base is then added thereto.

The alkoxycarbonylation (carbamation) of the α-aminohalomethylketone here referred to is a novel process, and the procedure 1 is also a novel process. Especially when tert-butoxycarbonylation is conducted, it is advisable to follow the procedure 1 because tert-butoxycarbonyl chloride or di-tert-butyl dicarbonate as the protecting reagent is unstable to an acid. That is, the procedure 1 is quite an excellent method in the tert-butoxycarbonylation reaction of the α-aminohalomethylketone in particular.

In the α-aminohalomethylketone, it is advisable to use the above-described stable acid salt. Examples of an appropriate solvent for dissolving the acid salt can include water, methanol and ethanol, for example.

The amino group protecting reagent is not particularly limited. A reagent ordinarily used in the peptide synthesis can of course be used, and further an optional compound having a functional group such as an alkoxycarbonyl group, an acyl group or a sulfonyl group can be used for introducing an optional substituent.

Examples of the amino acid protecting reagent can include alkoxycarbonylation reagents such as methoxycarbonyl chloride, ethoxycarbonyl chloride, isopropoxycarbonyl chloride, tert-butoxycarbonyl chloride, benzyloxycarbonyl chloride, di-tert-butyl dicarbonate and tetrahydrofuran-3-yloxycarbonyl chloride, acylation reagents such as acetic anhydride, acetyl chloride, benzoyl chloride and 3-protected hydroxy-2-methylbenzoyl chloride, and sulfonylation reagents such as methanesulfonyl chloride, trifluoromethanesulfonyl chloride, benzenesulfonyl chloride and p-toluenesulfonyl chloride. As stated earlier,the protecting groups introduced with these protecting reagents are sometimes not eliminated according to the subsequent step or the desired compound.

Examples of the base include organic bases such as triethylamine, diisopropylethylamine, dicyclohexylmethylamine, N-methylmorpholine, N-ethylmorpholine, pyridine, 2,6-lutidine, 2,4,6-collidine, 4-picoline and N-ethylpiperidine, and inorganic bases such as sodium hydroxide, potassium hydroxide, sodium carbonate, potassium carbonate, sodium hydrogencarbonate, potassium hydrogencarbonate, disodium hydrogenphosphate and dipotassium hydrogenphosphate.

With respect to the reaction solvent, an appropriate solvent can be used according to the reagent. Examples thereof include water, methanol, ethanol, 2-propanol, tert-butanol, acetone, tetrahydrofuran, diethyl ether, tert-butylmethyl ether, ethyl acetate, isopropyl acetate, dichloromethane, chloroform, toluene and mixed solvents thereof. When mixed solvents are used, there are a single layer system and a two-layer system depending on a combination of solvents. It is especially preferable that the reaction is conducted with a two-layer system through stirring.

When the amino group protecting reagent and the base are mixed in an appropriate solvent and a solution of an α-aminohalomethylketone acid salt is then added thereto (procedure 1), sodium hydrogencarbonate, potassium hydrogencarbonate, triethylamine or diisopropylethylamine is preferably used as the base. Triethylamine and diisopropylethylamine are especially preferable. The amount of the base to be added to the solution of the protecting reagent is preferably between 0.8 and 1.2 equivalents, more preferably close to 1 equivalent based on an acid (including an acid participating in formation of a salt) present in the α-aminohalomethylketone acid salt solution.

The α-aminohalomethylketone solution is added to the solvent in which the protecting reagent is dissolved. The reaction time varies with the reagent used or the reaction temperature. For example, when the tert-butoxycarbonylation is conducted with di-tert-butyl dicarbonate, the reaction is completed at 40° C. in several minutes to 2 hours and at room temperature in several minutes to 10 hours.

When the solution of the amino group protecting reagent such as the alkoxycarbonylation reagent, the acylation reagent or the sulfonylation reagent and the solution of the α-aminohalomethylketone acid salt are mixed and the base is then added thereto (procedure 2), sodium hydrogencarbonate, potassium hydrogencarbonate, triethylamine or diisopropylethylamine is preferably used as the base. The amount of the base added at this time is preferably between 0.8 and 1.2 equivalents, more preferably close to 1 equivalent based on an acid (including an acid participating in the formation of a salt) present in the α-aminohalomethylketone acid salt solution.

The base is added by being dissolved in an appropriate solvent. The reaction time varies with the reagent used or the reaction temperature. When the benzyloxycarbonylation is conducted using benzyloxycarbonyl chloride and the reaction is conducted at room temperature, the reaction is completed in 10 minutes to 2 hours.

Subsequently, the reaction solution is extracted with a solvent such as ethyl acetate, diethyl ether, toluene, isopropyl acetate, tert-butylmethyl ether, dichloromethane or chloroform, and the solution is concentrated (or distilled off) as required. Then, a solvent such as methanol, ethanol, 2-propanol, acetonitrile, tetrahydrofuran, hexane, heptane or acetone is added as required, the solution is heated to between 40° C. and 80° C., and crystallization is conducted by cooling to between −20° C. and room temperature or chromatography is conducted. In this manner, the N-protected-α-aminohalomethylketone (7) can be obtained as a solid. Further, the product may be used in the next reaction without purification by separation.

The N-protected-α-aminohalomethylketone represented by formula (7) is a known compound which is useful as, for example, an intermediate of a HIV protease inhibitor (refer to, for example, D. P. Getman et al., J. Med. Chem., 1993, 36, 288, Y. Okada et al., Chem. Pharm. Bull., 1988, 36, 4794, EP 346867 and P. Raddatz et al., J. Med. Chem., 1991, 34, 3267). It is known that the compound is converted into an intermediate in an advanced form by, for example, the following two-step known method (refer to, for example, D. P. Getman et al., J. Med. Chem., 1993,36,288, WO 96/23756 and Japanese Patent Laid-Open Nos. 99,947/1996 and 99,959/1996).

That is, it is possible that the N-protected-α-aminohalomethylketone represented by formula (7) is converted into an N-protected-β-aminoalcohol represented by formula (8) by a reduction reaction of a carbonyl group and this alcohol is further epoxidized easily under alkaline conditions to form an N-protected-β-aminoepoxide represented by formula (9).

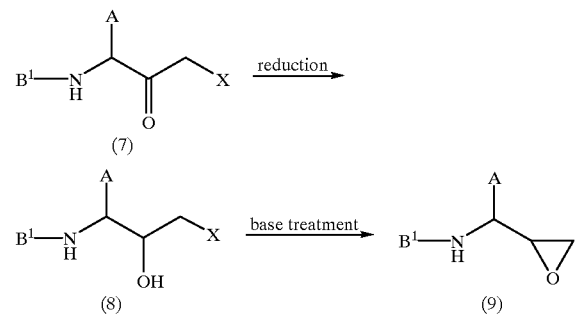

wherein A, X and $B^1$ are as defined above.

An example using sodium borohydride as a reducing agent is described below.

The amount of sodium borohydride added is not particularly limited. It is ordinarily used in an amount of 0.5 mol equivalent or more based on the starting material.

Examples of the reaction solvent can include protonic solvents such as water and alcohol. An alcohol or a mixed solvent of an alcohol and one or more of the other solvents is preferably used. Examples of the alcohol include methanol, ethanol, 1-propanol, 2-propanol, 1-butanol, 2-butanol and 1,2-dimethylpropanol. Methanol and ethanol are especially preferable. Further, as an alcohol, a combination of these is also available. Examples of the solvent used by being mixed with the alcohol include ethyl acetate, isopropyl acetate, dichloromethane, ether, tert-butylmethyl ether, tetrahydrofuran, 1,4-dioxane, benzene, toluene and water. Ethyl acetate, toluene and water are especially preferable.

The reaction temperature is not particularly limited. It is usually room temperature or less, preferably between −78° and room temperature, more preferably between −78° C. and 5° C. The reaction time is not particularly limited either. It is preferably between 10 minutes and 10 hours.

The reaction is usually conducted with stirring. After the completion of the reaction, the reaction is usually terminated with the addition of an acid. As the acid, hydrochloric acid, sulfuric acid, acetic acid, citric acid or a potassium hydrogensulfate aqueous solution can preferably be used. The amount of the acid used is not particularly limited. It is preferably used in an amount of 1 equivalent or more based on sodium borohydride.

Subsequently, the reaction solution is extracted with a solvent such as ethyl acetate, diethyl ether, toluene, isopropyl acetate, tert-butylmethyl ether, dichloromethane or chloroform, and the solution is concentrated (or distilled off) as required. Then, a solvent such as methanol, ethanol, 2-propanol, acetonitrile, tetrahydrofuran, hexane, heptane or acetone is added as required, the solution is heated to between 40° C. and 80° C., and crystallization is conducted by cooling to between −20° C. and room temperature or chromatography is conducted. In this manner, the N-protected-β-aminoalcohol can be obtained as a solid. Further, the crystals of the N-protected-β-aminoalcohol can also be obtained by concentrating the reaction solution as required, adding water thereto as required, directly conducting the crystallization by cooling under the above-mentioned conditions and washing the resulting crystals with water or the organic solvent.

The N-protected-β-aminoepoxide represented by formula (9) can be produced by treating the resulting N-protected-β-aminoalcohol represented by formula (8) with a base.

Examples of the base include potassium hydroxide, sodium hydroxide, potassium carbonate, sodium carbonate, sodium methoxide, sodium ethoxide, potassium tert-butoxide and sodium hydride. Sodium hydroxide and potassium carbonate are especially preferable. Examples of the reaction solvent include protonic solvents such as methanol, ethanol, 1-propanol, 2-propanol, 1-butanol, 2-butanol, 1,2-dimethylpropanol and water, and aprotic solvents such as acetone, tetrahydrofuran and acetonitrile. These are used either singly or in combination. Ethanol, a mixed solvent of 2-propanol and water, and a mixed solvent of ethanol and water are especially preferable.

The amount of the base used varies with the combination of the base and the solvent used. It is between 1 and 10 equivalents, preferably between 1 and 5 equivalents. The reaction temperature also varies with the combination of the base and the solvent used. It is between −10 and 80° C., preferably between 0 and 60° C. The reaction time is not particularly limited, and it is preferably between 10 minutes and 50 hours.

The reaction is usually conducted with stirring. After the completion of the reaction, the reaction may be terminated with the addition of an acid. As the acid, hydrochloric acid, sulfuric acid, acetic acid, citric acid or a potassium hydrogensulfate aqueous solution can preferably be used.

Subsequently, the reaction solution is extracted with a solvent such as ethyl acetate, diethyl ether, toluene, isopropyl acetate, tert-butylmethyl ether, dichloromethane or chloroform, and the solution is concentrated as required. Then, a solvent such as methanol, ethanol, 2-propanol, acetonitrile, tetrahydrofuran, hexane, heptane or acetone is added as required, the solution is heated to between room temperature and 50° C. as required, and crystallization is conducted by cooling to between −20° C. and room temperature or chromatography is conducted. In this manner, the N-protected-β-aminoepoxide can be obtained as a solid. Further, the crystals of the N-protected-β-aminoepoxide can also be obtained by concentrating the reaction solution as required, adding water thereto as required, directly conducting the crystallization by cooling under the above-mentioned conditions and washing the resulting crystals with water or the organic solvent.

The N-protected-β-aminoalcohol can also be formed from the α-aminohalomethylketone represented by formula (3) via the following novel route.

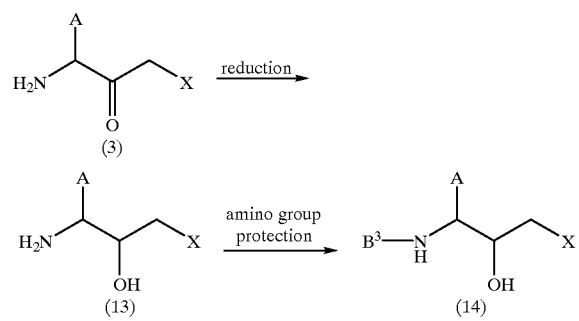

wherein A, $B^3$ and X are as defined above.

That is, the N-protected-β-aminoalcohol represented by formula (14) can be obtained by reducing the carbonyl group of the α-aminohalomethylketone represented by formula (3) to form a β-aminoalcohol represented by formula (13) and then protecting the amino group with a protecting group.

A reducing agent is previously dissolved or suspended in an appropriate solvent, and a solution of an acid salt of the α-aminohalomethylketone is added thereto.

The solvent in which the reducing agent is dissolved or suspended is not particularly limited. Protonic solvents such as water, methanol and ethanol are preferable.

Examples of the solvent in which the α-aminohalomethylketone is dissolved include water, methanol and ethanol. The α-aminohalomethylketone is preferably used in the form of a salt with an acid.

The reducing agent is not particularly limited. When it is reacted in an aqueous solution, sodium borohydride and sodium boron cyanohydride are especially preferable. The amount of the reducing agent added is not particularly limited. It is ordinarily used in an amount of 0.5 mol equivalent or more based on the starting material.

For inhibiting decomposition of the reducing agent with the acid, it is preferable to previously add a base along with the reducing agent. The amount of the base added to the solution of the reducing agent at this time is preferably between 1 and 2 equivalents, more preferably close to 1 equivalent based on the acid (including an acid participating in the formation of a salt) present in the acid salt solution of the α-aminohalomethylketone.

Examples of the base include sodium hydroxide, potassium hydroxide, sodium carbonate, potassium carbonate, sodium hydrogencarbonate and potassium hydrogencarbonate.

The reaction time is not particularly limited. When, for example, sodium borohydride is used, the reaction is conducted preferably at −20° C. to 100° C., especially preferably at 0° C. to room temperature.

The reaction is usually conducted with stirring. After the completion of the reaction, the reaction is terminated with the addition of an acid. As the acid, hydrochloric acid, sulfuric acid, acetic acid, citric acid or a potassium hydrogensulfate aqueous solution can preferably be used. The amount of the acid used is not particularly limited. It is preferably used in an amount of 1 equivalent or more based on sodium borohydride.

An insoluble matter is filtered off with the addition of an alcohol, and thereafter, crystallization (for example, crystallization by cooling or crystallization by concentration) is conducted from an alcohol or a mixed solvent of an alcohol and one or more of other solvents under appropriate conditions, whereby a β-aminoalcohol can be obtained as a salt. Preferable examples of the alcohol include methanol, ethanol and 2-propanol. Examples of the solvent used by being mixed with the alcohol include ethyl acetate, isopropyl acetate, dichloromethane, diethyl ether, tert-butylmethyl ether, tetrahydrofuran, 1,4-dioxane, benzene, toluene and water.

The β-aminoalcohol represented by formula (13) is a known compound which is useful as, for example, an intermediate of a HIV protease inhibitor (refer to, for example, P. L. Beaulieu et al., J. Org. Chem., 1996, 61, 3635). It is known that the compound is converted into an intermediate in an advanced form through, for example, the following two-step known reaction.

That is, it is possible that the β-aminoalcohol represented by formula (13) is converted into the N-protected-β-aminoalcohol represented by formula (14) by protecting the amino group in the foregoing manner and this alcohol is easily epoxidized under alkaline conditions as described above to form the N-protected-β-aminoepoxide represented by formula (15).

In the process of the invention, the protecting group such as the alkoxycarbonyl group, the acyl group or the sulfonyl group can be introduced into the α-aminohalomethylketone represented by formula (3) at good efficiency. That is, it is a general-purpose excellent process which can introduce a protecting group suited to a process for synthesis of various medical compounds.

The compound in the invention also includes a racemic compound and both optically active compounds. When an optically active amino acid ester is here used as the amino acid ester of formula (4), the compound of formula (3) obtained by the process of the invention maintains its optical activity. Further, in the compounds of formulas (7) to (9) and (13) to (15) produced from the compound of formula (3), the optical activity can also be maintained.

In view of the foregoing, the process of the invention is a process which is quite useful as a process for synthesis of medical intermediate compounds.

The invention is illustrated more specifically by referring to the following Examples. Of course, the invention is not limited to these Examples at all.

Example 1

Process for producing N-(diphenylmethylene)-L-phenylalanine methyl ester

L-phenylalanine methyl ester hydrochloride (5.95 g) and benzophenonimine (5.00 g) were added to methylene chloride (100 ml), and the mixture was stirred overnight at room temperature. The solid was filtered off from the reaction solution, and the solvent was distilled off under reduced pressure. Then, diethyl ether (100 ml) was added to the residue. The solid was filtered off again, and the ether layer was then washed with water (100 ml), and dried over anhydrous magnesium sulfate. After magnesium sulfate was removed, the ether solution was concentrated to obtain desired N-(diphenylmethylene)-L-phenylalanine methyl ester (9.44 g) in a yield of 99.6%.

$^1$H-NMR(CDCl$_3$) δppm: 3.17 (dd, J=9.0, 13.5 Hz, 1H), 3.27 (dd, J=3.9, 13.5 Hz, 1H), 3.70 (s, 3H), 4.27 (dd, J=3.9, 9.0 Hz, 1H), 6.58 (d, J=9.0 Hz, 2H), 7.01–7.04 (m, 2H), 7.16–7.19 (m, 3H), 7.25–7.41 (m, 6H), 7.58 (d, J=6.0 Hz, 2H)

Example 2

Process for producing (3S)-1-chloro-3-(diphenylmethylene)amino-4-phenyl-2-butanone N-(diphenylmethylene)-L-phenylalanine methyl ester (3.35 g) and bromochloromethane (0.83 ml) were added to dehydrated tetrahydrofuran (97 ml), and the mixture was cooled to −78° C. Then, a 1.53 M n-butyllithium hexane solution (8.3 ml) was added thereto. The mixture was stirred for 35 minutes. A saturated aqueous solution of ammonium chloride was added to the reaction solution to terminate the reaction. The resulting reaction solution was extracted twice with ethyl acetate at room temperature. The ethyl acetate layer was then washed with a saturated aqueous solution of sodium chloride, and dried over anhydrous magnesium sulfate. After magnesium sulfate was removed, the ethyl acetate solution was concentrated to obtain desired (3S)-1-chloro-3-(diphenylmethylene)amino-4-phenyl-2-butanone (3.52 g) in a yield of 99.7%.

$^1$H-NMR(CDCl$_3$) δppm: 3.07 (dd, J=8.8, 13.8 Hz, 1H), 3.15 (dd, J=13.8, 4.2 Hz, 1H), 4.31 (dd, J=4.2, 8.8 Hz, 1H), 4.38 (d, J=17.1 Hz, 1H), 4.58 (d, J=17.1 Hz, 1H), 6.43 (d, J=9.9 Hz, 2H), 6.99–7.04 (m, 2H), 7.18–7.4 (m, 9H), 7.60 (d, J=9.1 Hz, 2H)

$[α]_D^{25}$=+8.5° (c=1, EtOH)

Example 3

Process for producing (3S)-3-amino-1-chloro-4-phenyl-2-butanone hydrochloride (3S)-1-chloro-3-(diphenylmethylene)amino-4-phenyl-2-butanone (1.85 g) and 2 N hydrochloric acid (5.1 ml) were added to tetrahydrofuran (10 ml), and the mixture was stirred overnight. After the solvent was distilled off under reduced pressure, isopropyl acetate was added to the residue, and the mixture was extracted twice with water. The resulting aqueous solution was analyzed by HPLC, and it was identified that desired (3S)-3-amino-1-chloro-4-phenyl-2-butanone hydrochloride (0.94 g) was obtained in a yield of 79%. The analysis was conducted with an optically active column, and it was identified that the optical purity was >99.5%e.e.

Further, for obtaining various spectrum data, a part of the resulting aqueous solution was concentrated under reduced pressure, and ethanol was added thereto. The solvent was distilled off again under reduced pressure, and salts were distilled off. The filtrate was concentrated, and then crystallized from ethanol and tert-butylmethyl ether to obtain the crystals of (3S)-3-amino-1-chloro-4-phenyl-2-butanone hydrochloride.

$^1$H-NMR(d6-DMSO) δppm: 3.04 (dd, J=7.1, 15.2 Hz, 1H), 3.22 (dd, J=7.1, 15.2 Hz, 1H), 4.54 (t, J=7.1 Hz, 1H), 4.58 (d, J=17.3 Hz, 1H), 4.70 (d, J=17.3 Hz, 1H), 7.28–7.41 (m, 5H), 8.37 (bs, 3H)

mass spectrum m/e: 198.0 (MH+)

$[α]_D^{25}$=+30.2° (c=0.5, H$_2$O)

Example 4

Process for producing N-(p-methoxyphenylmethylene)-L-phenylalanine methyl ester

L-phenylalanine methyl ester hydrochloride (4.31 g), p-anisaldehyde (2.45 ml), anhydrous magnesium sulfate (5.19 g) and triethylamine (2.9 ml) were added to methylene chloride (200 ml), and the mixture was stirred overnight at room temperature. The solid was filtered off from the reaction solution, and the solvent was distilled off under reduced pressure. Then, ethyl acetate (150 ml) was added to the residue. The solid was separated again by filtration, and the solvent was distilled off under reduced pressure to quantitatively obtain desired N-(p-methoxyphenylmethylene)-L-phenylalanine methyl ester (5.94 g).

$^1$H-NMR(CDCl$_3$) δppm: 3.13 (dd, J=9.2, 13.8 Hz, 1H), 3.36 (dd, J=5.0, 13.8 Hz, 1H), 3.73 (s, 3H), 3.83 (s, 3H), 4.13 (dd, J=5.0, 9.2 Hz, 1H), 6.86–6.92 (m, 2H), 7.14–7.26 (m, 5H), 7.64 (d, J=12.0 Hz, 2H), 7.85 (s, 1H) mass spectrum m/e: 298.3 (MH+)

Example 5

Process for producing (S)-3-amino-1-chloro-4-phenyl-2-butanone hydrochloride

N-(p-methoxyphenylmethylene)-L-phenylalanine methyl ester (2.00 g) and bromochloromethane (0.57 ml) were added to dehydrated tetrahydrofuran (67 ml), and the mixture was cooled to −78° C. Then, a 1.53 M n-butyllithium hexane solution (5.7 ml) was added thereto. The mixture was stirred for 20 minutes. A part of the reaction solution was taken out, and the reaction solution was added to a neutral phosphate buffer (pH =6.86) to terminate the reaction. At the same time, 2 N hydrochloric acid was added to the remaining reaction solution to terminate the reaction. The part of the reaction solution treated with the phosphate buffer was extracted three times with ethyl acetate. The resulting ethyl acetate layer was dried over anhydrous magnesium sulfate, and magnesium sulfate was removed. The solvent was distilled off under reduced pressure to obtain oil. This was analyzed by NMR, and it was identified to be (3S)-1-chloro-3-(p-methoxyphenylmethylene)amino-4-phenyl-2-butanone, a desired intermediate. After the completion of the NMR analysis, this was mixed with the reaction solution treated with 2 N hydrochloric acid, and the solvent was distilled off under reduced pressure. Then, isopropyl acetate was added to the residue, and the mixture was extracted twice with water. The resulting aqueous solution was analyzed by HPLC, and it was identified that desired (S)-3-amino-1-chloro-4-phenyl-2-butanone hydrochloride (1.30 g) was obtained in a yield of 82%.

It was identified by HPLC analysis using an optically active column that the optical purity of (S)-3-amino-1-chloro-4-phenyl-2-butanone hydrochloride obtained here was >99.5%e.e.

The NMR data of (3S)-1-chloro-3-(p-methoxyphenylmethylene)amino-4-phenyl-2-butanone is described below.

$^1$H-NMR(CDCl$_3$) δppm: 3.01 (dd, J=9.2, 13.8 Hz, 1H), 3.28 (dd, J=4.9, 13.8 Hz, 1H), 3.83 (s, 3H), 4.18 (dd, J=4.9, 9.2 Hz, 1H), 4.40 (d, J=17.1 Hz, 1H), 4.54 (d, J=17.1 Hz, 1H), 6.89 (d, J=12.0 Hz, 2H), 7.14–7.26 (m, 5H), 7.64 (d, J=12.0 Hz, 2H), 7.85 (s, 1H)

Example 6

Process for producing N-(phenylmethylene)-L-phenylalanine methyl ester

L-phenylalanine methyl ester hydrochloride (4.31 g), benzaldehyde (2.05 ml), anhydrous magnesium sulfate (5.19 g) and triethylamine (2.90 ml) were added to methylene chloride (200 ml), and the mixture was stirred overnight at room temperature. The solid was filtered off from the reaction solution, and the solvent was distilled off under reduced pressure. Then, ethyl acetate (150 ml) was added to the residue. The solid was separated again by filtration, and the solvent was distilled off under reduced pressure to obtain desired N-(phenylmethylene)-L-phenylalanine methyl ester (5.18 g) in a yield of 97.0%.

$^1$H-NMR(CDCl$_3$) δppm: 3.15 (dd, J=8.9, 14.5 Hz, 1H), 3.38 (dd, J=5.0, 14.5 Hz, 1H), 3.74 (s, 3H), 4.17 (dd, J=5.0, 8.9 Hz, 1H), 7.14–7.25 (m, 5H), 7.34–7.44 (m, 3H), 7.67–7.71 (m, 2H), 7.90 (s, 1H)

mass spectrum m/e: 268.2 (MH+)

Example 7

Process for producing N-(phenylmethylene)-L-phenylalanine methyl ester

L-phenylalanine methyl ester hydrochloride (120.00 g), benzaldehyde (56.5 ml), anhydrous sodium sulfate (158.07 g) and triethylamine (77.5 ml) were added to tert-butylmethyl ether (480 ml), and the mixture was stirred overnight at 5° C. The solid was filtered off from the reaction solution, and the solvent was distilled off under reduced pressure. Then, n-hexane was added, and the solvent was distilled off again under reduced pressure. To the concentrate was added n-hexane, and the crystallization was conducted by cooling with ice to obtain desired N-(phenylmethylene)-L-phenylalanine methyl ester (126.01 g) in a yield of 85.0%. Further, the mother liquor was concentrated under reduced pressure, and the concentrate was crystallized by cooling with ice to obtain N-(phenylmethylene)-L-phenylalanine methyl ester (13.86 g) in a yield of 9%. Thus, the crystals of N-(phenylmethylene)-L-phenylalanine methyl ester were obtained in a total yield of 94%. A part of the resulting crystals were converted into a phenylalanine methyl ester. It was analyzed by HPLC using an optically active column, and identified to have the optical purity of >99.5%e.e.

Example 8

Process for producing (S)-3-amino-1-chloro-4-phenyl-2-butanone hydrochloride

N-(phenylmethylene)-L-phenylalanine methyl ester (2.05 g) and bromochloromethane (0.65 ml) were added to dehydrated tetrahydrofuran (60 ml), and the mixture was cooled to −78° C. Then, a 1.53 M n-butyllithium hexane solution (6.5 ml) was added, and the mixture was stirred for 30 minutes. 2 N hydrochloric acid was added to the reaction solution to terminate the reaction. Isopropyl acetate was added, and the mixture was extracted twice with water. The resulting aqueous solution was analyzed by HPLC, and it was identified that desired (S)-3-amino-1-chloro-4-phenyl-2-butanone hydrochloride (1.35 g) was obtained in a yield of 75%.

It was identified by HPLC analysis using an optically active column that the optical purity of (S)-3-amino-1-chloro-4-phenyl-2-butanone hydrochloride obtained here was >93%e.e.

The aqueous solution containing (S)-3-amino-1-chloro-4-phenyl-2-butanone hydrochloride (1.23 g) from which the sample for analysis was excluded was concentrated under reduced pressure. Ethanol was added to the residue, and the solvent was distilled off again under reduced pressure. The salts were filtered off, and the filtrate was concentrated. The concentrate was then crystallized from ethanol and tert-butylmethyl ether to obtain crystals (0.61 g) of (3S)-1-chloro-3-amino-4-phenyl-2-butanone hydrochloride in a crystallization rate of 49%. Further, the mother liquor was concentrated under reduced pressure, and the concentrate was crystallized from ethanol and tert-butylmethyl ether to obtain crystals (0.37 g) of (3S)-1-chloro-3-amino-4-phenyl-2-butanone hydrochloride in a crystallization rate of 30%. Thus, the crystals of (3S)-1-chloro-3-amino-4-phenyl-2-butanone hydrochloride were obtained in a total crystallization rate of 79%.

Example 9

Process for producing (S)-3-amino-1-chloro-4-phenyl-2-butanone hydrochloride

N-(phenylmethylene)-L-phenylalanine methyl ester (2.03 g) and bromochloromethane (0.65 ml) were added to dehydrated tetrahydrofuran (60 ml), and the mixture was cooled to −78° C. Then, a 1.53 M n-butyllithium hexane solution (6.5 ml) was added, and the mixture was stirred for 30 minutes. 2 N hydrochloric acid was added to the reaction solution to terminate the reaction. Then, tert-butylmethyl ether was added, and the mixture was extracted twice with water. The resulting aqueous solution was analyzed by HPLC, and it was identified that desired (S)-3-amino-1-chloro-4-phenyl-2-butanone hydrochloride (1.39 g) was obtained in a yield of 78%. It was identified by HPLC analysis using an optically active column that the optical purity of (S)-3-amino-1-chloro-4-phenyl-2-butanone hydrochloride obtained here was >98%e.e.

Example 10

Process for producing (S)-3-amino-1-chloro-4-phenyl-2-butanone hydrochloride

N-(phenylmethylene)-L-phenylalanine methyl ester (2.04 g) and bromochloromethane (0.65 ml) were added to a mixed solution of dehydrated tetrahydrofuran (30 ml) and dehydrated toluene (30 ml), and the mixture was cooled to −78° C. Then, a 1.53 M n-butyllithium hexane solution (6.5 ml) was added, and the mixture was stirred for 45 minutes. 2 N hydrochloric acid was added to the reaction solution to terminate the reaction and tert-butylmethyl ether was added. The solution was extracted twice with water. The resulting aqueous solution was analyzed by HPLC, and it was identified that desired (S)-3-amino-1-chloro-4-phenyl-2-butanone hydrochloride (1.50 g) was obtained in a yield of 84%. It was identified by the HPLC analysis using an optically active column that the optical purity of (S)-3-amino-1-chloro-4-phenyl-2-butanone hydrochloride obtained here was >98%e.e.

Example 11

Process for producing (S)-3-amino-1-chloro-4-phenyl-2-butanone hydrochloride

N-(phenylmethylene)-L-phenylalanine methyl ester (2.0 g) and chloroiodomethane (0.71 ml) were added to a mixed solution of dehydrated tetrahydrofuran (7.4 ml) and dehydrated toluene (7.4 ml), and the mixture was cooled to −78° C. Then, a 1.53 M n-butyllithium hexane solution (6.5 ml) was added, and the mixture was stirred for 70 minutes. 2 N hydrochloric acid was added to the reaction solution to terminate the reaction. Then, the solution was extracted twice with water.

The resulting aqueous solution was analyzed by HPLC, and it was identified that desired (S)-3-amino-1-chloro-4-phenyl-2-butanone hydrochloride (0.977 g) was obtained in a yield of 56%.

Example 12

Process for producing (3S)-3-tert-butoxycarbonylamino-1-chloro-4-phenyl-2-butanone Di-tert-butyl dicarbonate (1.39 g) and sodium hydrogencarbonate (0.34 g) were dissolved in a 50% methanol aqueous solution (22 ml), and an aqueous solution of (3S)-3-amino-1-chloro-4-phenyl-2-butanone hydrochloride (0.94 g) was added thereto. The mixture was stirred at 40° C. for 1.5 hours. The reaction solution was extracted twice with ethyl acetate, the resulting ethyl acetate layer was dried over anhydrous magnesium sulfate, and magnesium sulfate was removed. The ethyl acetate layer was concentrated, and crystallized by adding hexane thereto. Crystals precipitated were collected by filtration, and dried to obtain (3S)-3-tert-butoxycarbonylamino-1-chloro-4-phenyl-2-butanone (0.84 g) in a yield of 70%.

Further, the crystals obtained and the reaction solution were analyzed by HPLC using an optically active column, and it was identified that the optical purity thereof was >99.5%e.e., and that a series of reactions proceeded while maintaining the optical purity of L-phenylalanine methyl ester hydrochloride.

$^1$H-NMR(CDCl$_3$) δppm: 1.41 (s, 9H), 3.00 (dd, J=6.9, 13.8 Hz), 3.08 (dd, J=6.9, 13.8 Hz, 1H), 3.98 (d, J=16.2 Hz, 1H), 4.17 (d, J=16.2 Hz, 1H), 4.68 (q, J=6.9 Hz, 1H), 5.02 (bd, J=6.9 Hz, 1H), 7.16 (m, 2H), 7.26–7.36 (m, 3H)

mass spectrum m/e: 296.1 (M−H−)

$[\alpha]_D^{25}$=−55.7° (c=1, EtOH)

Example 13

Process for producing (3S)-3-tert-butoxycarbonylamino-1-chloro-4-phenyl-2-butanone Di-tert-butyl dicarbonate (85.8 mg) and triethylamine (29.1 mg) were dissolved in methylene chloride (2.6 ml), and an aqueous solution of (3S)-3-amino-1-chloro-4-phenyl-2-butanone hydrochloride (61.4 mg) in water (2.6 ml) was added thereto dropwise. The mixture was stirred at room temperature for 1 hour, then heated at 40° C., and further reacted for 1.5 hours. After the reaction solution was cooled to room temperature, a sodium chloride aqueous solution was added thereto, and the mixture was extracted twice with ethyl acetate. The resulting ethyl acetate layer was analyzed by HPLC, and it was identified that (3S)-3-tert-butoxycarbonylamino-1-chloro-4-phenyl-2-butanone (66.3 mg) was obtained in a yield of 85%.

Example 14

Process for producing (3S)-3-tert-butoxycarbonylamino-1-chloro-4-phenyl-2-butanone Di-tert-butyl dicarbonate (85.8 mg) and triethylamine (29.1 mg) were dissolved in ethyl acetate (2.6 ml), and an aqueous solution of (3S)-3-amino-1-chloro-4-phenyl-2-butanone hydrochloride (61.4 mg) in water (2.6 ml) was added thereto dropwise. The mixture was stirred at room temperature for 1 hour, then heated at 40° C., and further reacted for 1.5 hours. After the reaction solution was cooled to room temperature, a sodium chloride aqueous solution was added thereto, and the mixture was extracted twice with ethyl acetate. The resulting ethyl acetate layer was analyzed by HPLC, and it was identified that (3S)-3-tert-butoxycarbonylamino-1-chloro-4-phenyl-2-butanone (66.3 mg) was obtained in a yield of 92%.

Example 15

Process for producing (3S)-3-tert-butoxycarbonylamino-1-chloro-4-phenyl-2-butanone Di-tert-butyl dicarbonate (4.64 g) and triethylamine (5.28 ml) were dissolved in toluene (81.9 ml), and an aqueous solution (45.60 g) of (3S)-3-amino-1-chloro-4-phenyl-2-butanone hydrochloride (3.83 g) was added thereto dropwise over 10 minutes. The solution was stirred at room temperature for 1 hour, then heated at 40° C., and further reacted for 1 hour. After the reaction solution was cooled to room temperature, the aqueous layer was separated. The resulting toluene layer was washed with 2 N hydrochloric acid and with a saturated aqueous solution of sodium chloride, and dried over anhydrous magnesium sulfate. Then, magnesium sulfate was removed. The resulting toluene layer was analyzed by HPLC, and it was identified that (3S)-3-tert-butoxycarbonylamino-1-chloro-4-phenyl-2-butanone (3.94 g) was obtained in a yield of 81%. The solvent was distilled off under reduced pressure, and n-hexane and 2-propanol were added to the residue. The solution was heated to 50° C. to form a uniform solution. Thereafter, this solution was cooled to room temperature, stirred for 1 hour, further cooled to 5° C., and stirred for 1 hour. Crystals precipitated were collected by filtration, and dried to obtain (3S)-3-tert-butoxycarbonylamino-1-chloro-4-phenyl-2-butanone (2.98 g) in a crystallization rate of 75%.

Example 16

Process for producing (3S)-3-tert-butoxycarbonylamino-1-chloro-4-phenyl-2-butanone Di-tert-butyl dicarbonate (1.20 g) and diisopropylethylamine (2.65 ml) were dissolved in toluene (11.5 ml), and an aqueous solution (11.27 g) of (3S)-3-amino-1-chloro-4-phenyl-2-butanone hydrochloride (1.00 g) was added thereto dropwise over 35 minutes. The mixture was reacted overnight at room temperature by being stirred, and the aqueous layer was then separated. The resulting toluene layer was washed with an aqueous solution of 1 mol/liter of citric acid and with water. The resulting toluene layer was analyzed by HPLC, and it was identified that (3S)-3-tert-butoxycarbonylamino-1-chloro-4-phenyl-2-butanone (0.95 g) was obtained in a yield of 75%.

Example 17

Process for producing (3S)-3-benzyloxycarbonylamino-1-chloro-4-phenyl-2-butanone (3S)-3-amino-1-chloro-4-phenyl-2-butanone hydrochloride (100 mg) was dissolved in water (4.3 ml), and a toluene solution (5.3 ml) of benzyl chloroformate (0.794 ml) was added thereto. An aqueous solution (1.0 ml) of sodium hydrogencarbonate (71.9 mg) was further added dropwise thereto while being stirred. After the mixture was reacted at room temperature for 50 minutes while being stirred, the aqueous layer was separated. The resulting toluene layer was analyzed by HPLC, and it was identified that (3S)-3-benzyloxycarbonylamino-1-chloro-4-phenyl-2-butanone (118 mg) was obtained in a yield of 83%.

Example 18

Process for producing (3S)-3-methoxycarbonylamino-1-chloro-4-phenyl-2-butanone (3S)-3-amino-1-chloro-4-phenyl-2-butanone hydrochloride (2.0 mg) was dissolved in water (34 ml), and a toluene solution (50 ml) of methyl chloroformate (0.858 ml) was added thereto. An aqueous solution (15 ml) of sodium hydrogencarbonate (1.44 g) was further added dropwise thereto while being stirred. The mixture was reacted at room temperature for 1 hour while being stirred, and then extracted twice with toluene and twice with ethyl acetate. The organic layers were combined, and the solvents were distilled off under reduced pressure. To the residue were added n-hexane and 2-propanol. The resulting solution was heated at 50° C. to form a uniform solution. This solution was then cooled to 10° C., and crystals precipitated were collected by filtration. The crystals were washed with cold 2-propanol (6 ml), and then dried to obtain (3S)-3-methoxycarbonylamino-1-chloro-4-phenyl-2-butanone (1.70 g) in a yield of 78%.

$^1$H-NMR(CDCl$_3$) δppm: 2.97–3.14 (m, 2H), 3.66 (s, 3H), 3.98 (d, J=16.0 Hz, 1H), 4.15 (d, J=16.0 Hz, 1H), 4.75 (q, J=7.2 Hz, 1H), 5.21 (bd, 1H), 7.12–7.18 (m, 2H), 7.23–7.37 (m, 3H)

Example 19

Process for producing (2S,3S)-3-tert-butoxycarbonylamino-1-chloro-2-hydroxy-4-phenylbutane (3S)-3-tert-butoxycarbonylamino-1-chloro-4-phenyl-2-butanone (0.57 g) was added to a mixed solution of methanol (9 ml) and methylene chloride (9 ml), and sodium borohydride (92 mg) was charged in divided portions while being cooled with ice. The mixture was stirred for 1 hour. To the reaction solution was added acetic acid (0.59 ml) to terminate the reaction. Water was added, and the mixture was extracted twice with isopropyl acetate. The resulting isopropyl acetate solution was washed twice with a 5% sodium hydrogencarbonate aqueous solution and once with a saturated aqueous solution of sodium chloride.

The thus-obtained isopropyl acetate solution was analyzed by HPLC, and it was identified that 3-tert-butoxycarbonylamino-1-chloro-2-hydroxy-4-phenylbutane (0.57 g) was obtained in a yield of 83%. A ratio of the desired product (2S,3S) and its isomer (2R,3S) formed was (2S,3S):(2R,3S)=83.2:16.8.

A part of the isopropyl acetate solution of (2S,3S)-3-tert-butoxycaronylamino-1-chloro-2-hydroxy-4-phenylbutane obtained here was taken out, and the solvent was distilled off under reduced pressure. To the residue was added ethyl acetate, the mixture was heat-dissolved, and n-hexane was added thereto. The crystallization was conducted by cooling with ice to obtain crystals of (2S,3S)-3-tert-butoxycarbonylamino-1-chloro-2-hydroxy-4-phenylbutane.

$^1$H-NMR(CDCl$_3$) δppm: 1.37 (s, 9H), 2.85–2.98 (m, 1H), 3.00 (dd, J=5.8, 13.9 Hz, 1H), 3.16 (bs, 1H), 3.59 (dd, J=11.6, 17.4 Hz, 1H), 3.59–3.71 (m, 1H), 3.77–3.97 (bm, 2H), 4.57 (bs, 1H), 7.19–7.35 (m, 5H)

mass spectrum m/e: 322 (M+Na+)

$[α]_D^{20}$=−23.6° (c=0.5, CH$_2$Cl$_2$)

Example 20

Process for producing (2S,3S)-3-tert-butoxycarbonylamino-1-chloro-2-hydroxy-4-phenylbutane Ethyl acetate (4.2 ml) and ethanol (16.7 ml) were added to (3S)-3-tert-butoxycarbonylamino-1-chloro-4-phenyl-2- butanone (2.08 g), and sodium borohydride (133 mg) was charged in divided portions at −10° C. The mixture was stirred for 1 hour and 40minutes. To the reaction solution was added acetic acid (0.40 ml) to terminate the reaction. The solution was heated at 60° C. over 1 hour, and further stirred at 60° C. for 30 minutes. Subsequently, the reaction solution was cooled to −10° C. over 1 hour and 50 minutes, and further stirred at −10° C. for 6 hours. Crystals obtained were collected by filtration, washed with water of 0° C., and dried under reduced pressure to obtain desired (2S,3S)-3-tert-butoxycarbonylamino-1-chloro-2-hydroxy-4-phenylbutane (1.52 g). The dry crystals were analyzed by HPLC, and found to be crystals having a quality of (2S,3S):(2R,3S)=98.5:1.5.

Example 21

Process for producing (2S,3S)-3-amino-1-chloro-2-hydroxy-4-phenylbutane hydrochloride N-(phenylmethylene)-L-phenylalanine methyl ester (1.39 g) and bromochloromethane (0.44 ml) were added to a mixed solution of dehydrated tetrahydrofuran (15 ml) and dehydrated toluene (15 ml), and the mixture was cooled to −78° C. Then, a 1.53 M n-butyllithium hexane solution (4.4 ml) was added, and the mixture was stirred for 40 minutes. 2 N hydrochloric acid (6.5 ml) was added to the reaction solution to terminate the reaction. Tert-butylmethyl ether was added, and the mixture was extracted twice with water. The resulting aqueous solution was analyzed by HPLC, and it was identified that desired (S)-3-amino-1-chloro-4-phenyl-2-butanone hydrochloride (0.99 g) was obtained in a yield of 82%.

It was identified by HPLC analysis using an optically active column that the optical purity of (S)-3-amino-1-chloro-4-phenyl-2-butanone hydrochloride obtained here was >98%e.e.

After this aqueous solution was concentrated to an amount of ⅓ under reduced pressure, the concentrate was added dropwise to a solution of a 1 N sodium hydroxide aqueous solution (13 ml), methanol (13 ml) and sodium borohydride (0.17 g) over 25 minutes while being cooled with ice, and the mixture was then stirred for 1 hour. To the reaction solution was added 2 N hydrochloric acid (9.5 ml) to terminate the reaction. After the reaction, the solution was analyzed by HPLC, and it was identified that 3-amino-1-chloro-2-hydroxy-4-phenylbutane hydrochloride (1.00 g) was obtained in a yield of 100%. A ratio of the desired product (2S,3S) and its isomer (2R,3S) formed was (2S,3S):(2R,3S) =82.2:17.8.

For obtaining various spectrum data, a part of the solution after the reduction was sampled, and concentrated under reduced pressure, and ethanol was then added thereto. The solvent was distilled off again under reduced pressure, and salts were filtered off. The filtrate was concentrated, and then crystallized from ethanol and tert-butylmethyl ether to obtain (2S,3S)-3-amino-1-chloro-2-hydroxy-4-phenylbutane hydrochloride.

$^1$H-NMR(d6-DMSO) δppm: 2.85 (dd, J=7.6, 14.4 Hz, 1H), 3.00 (dd, J=6.2, 14.4 Hz, 1H), 3.47–3.57 (m, 2H), 3.65 (dd, J=5.1, 11.3 Hz, 1H), 3.93–4.01 (m, 1H), 6.13 (d, J=5.6 Hz, 1H), 7.23–7.38 (m, 5H), 8.16 (bs, 3H)

mass spectrum m/e: 200 (MH+)

$[\alpha]_D^{20}$=−45.0° (c=0.9, 0.5 N HCl)

Example 22

Process for producing (2S,3S)-3-tert-butoxycarbonylamino-1-chloro-2-hydroxy-4-phenylbutane The solution containing 3-amino-1-chloro-2-hydroxy-4-phenylbutane hydrochloride (0.96 g, (2S,3S):(2R,3S)= 82.2:17.8) obtained in Example 21 after the reduction was concentrated to an amount of ⅕ under reduced pressure. Subsequently, water (3 ml), methanol (19 ml) and a 5% sodium hydrogencarbonate aqueous solution were added, and a methanol (10 ml) solution of di-tert-butyl dicarbonate (1.07 g) was then added. The mixture was stirred at room temperature for 2 hours. To the reaction solution was added 2 N hydrochloric acid, and the mixture was extracted twice with isopropyl acetate. The resulting isopropyl acetate layer was washed with a saturated aqueous solution of sodium chloride. The thus-obtained isopropyl acetate layer was analyzed by HPLC, and it was identified that 3-tert-butoxycarbonylamino-1-chloro-2-hydroxy-4-phenylbutane (0.82 g) was obtained in a yield of 68%. A ratio of the desired product (2S,3S) and its isomer (2R,3S) formed was (2S,3S):(2R,3S)=74.5:25.5.

Example 23

Process for producing (2S,3S)-3-tert-butoxycarbonylamino-1,2-epoxy-4-phenylbutane (2S,3S)-3-tert-butoxycarbonylamino-1-chloro-2-hydroxy-4-phenylbutane (0.40 g) and potassium carbonate (0.37 g) were added to methanol (8 ml), and the mixture was stirred at room temperature for 6 hours. The inorganic salt was filtered off from the reaction solution, and the filtrate was then concentrated under reduced pressure. To the residue was added water, and the solution was extracted with methylene chloride. The resulting methylene chloride layer was washed with a 20% citric acid aqueous solution, and the solvent was then distilled off under reduced pressure. Ethyl acetate (2 ml) was added to the residue. The mixture was heat-dissolved, and crystallized by being cooled to room temperature. Further, n-hexane (4 ml) was added thereto, and the resulting mixture was stirred while being cooled with ice. Crystals were separated, and dried to obtain the crystals (0.30 g) of desired (2S,3S)-3-tert-butoxycarbonylamino-1,2-epoxy-4-phenylbutane in a yield of 85%.

$^1$H-NMR(CDCl$_3$) δppm: 1.38 (s, 9H), 2.73–2.81 (m, 2H), 2.84–3.01 (m, 3H), 3.69 (bs, 1H), 4.54 (d, J=8.2 Hz, 1H), 7.21–7.31 (m, 5H)

mass spectrum m/e: 286 (M+Na+)

$[\alpha]_D^{20}$=−15.4° (c=2.2, CH$_2$Cl$_2$)

Example 24

Process for producing (2S,3S)-3-tert-butoxycarbonylamino-1,2-epoxy-4-phenylbutane (2S,3S)-3-tert-butoxycarbonylamino-1-chloro-2-hydroxy-4-phenylbutane (5.29 g) and potassium carbonate (4.88 g) were added to an ethanol:water (97:3) mixed solution (106 ml). The mixture was stirred at 33° C. for 7 hours, and a 10% citric acid aqueous solution(67.8 g)was added there to. After ethanol was distilled off under reduced pressure, toluene (93 ml) was added to conduct extraction. Further, the organic layer was washed with water (93 ml), and then concentrated. To the residue was added a heptane-:toluene (4:1) mixture (112 ml). The heating was conducted at 50° C. over 1 hour, and the stirring was further conducted at 50° C. for 1 hour. Subsequently, cooling was conducted to −10° C. over 5 hours, and stirring was further conducted at −10° C. for 8 hours. Crystals were collected by filtration, washed with heptane, and then dried under reduced pressure to obtain desired (2S,3S)-3-tert-butoxycarbonylamino-1,2-epoxy-4-phenylbutane (4.39 g) in a yield of 95%.

Example 25

Process for producing (2S,3S)-3-tert-butoxycarbonylamino-1,2-epoxy-4-phenylbutane (2S,3S)-3-tert-butoxycarbonylamino-1-chloro-2-hydroxy-4-phenylbutane (3.57 g) and potassium carbonate (3.29 g) were added to an ethanol:water (97:3) mixed solution (35.7 ml). The mixture was stirred at 27° C. for 22 hours and further at 33° C. for 4 hours. A 11.3% citric acid aqueous solution (40.3 g) was added thereto, and the cooling was then conducted to −10° C. Crystals were collected by filtration, washed with water (35.7 ml), and dried under reduced pressure to obtain desired (2S,3S)-3-tert-butoxycarbonylamino-1,2-epoxy-4-phenylbutane (2.88 g) in a yield of 95%.

Example 26

Process for producing (2S,3S)-3-tert-butoxycarbonylamino-1,2-epoxy-4-phenylbutane 2-Propanol (2.4 ml) was added to (2S,3S)-3-tert-butoxycarbonylamino-1-chloro-2-hydroxy-4-phenylbutane (300 mg). After the mixture was cooled to 4° C., an aqueous solution (0.375 ml) of 4 mols/liter of sodium hydroxide and water (0.225 ml) were added thereto, and the mixture was stirred at 4° C. for 7 hours. After a 13.7% citric acid aqueous solution (695 mg) was added thereto, the mixture was extracted with tert-butylmethyl ether. The resulting organic layer was washed with water. It was identified by HPLC analysis that desired (2S,3S)-3-tert-butoxycarbonylamino-1,2-epoxy-4-phenylbutane (230 mg) was obtained in a yield of 87%.

According to the invention, an α-aminohalomethylketone, an N-protected-α-aminohalomethylketone and related products thereof can be produced from an α-amino acid ester in good yields at low costs, and various compounds useful as medical intermediates can be produced. Further, since the optical activity is maintained, it is especially useful for the production of medical intermediates having structures derived from optically active amino acids.

What is claimed is:

1. A process for producing an α-aminohalomethylketone represented by formula (3)

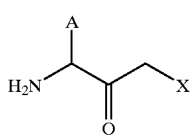

(3)

wherein
A represents an optionally substituted alkyl group having 1 to 10 carbon atoms, an optionally substituted aryl group having 6 to 15 carbon atoms, an optionally substituted aralkyl group having 7 to 20 carbon atoms, or a group in which heteroatom is contained in these carbon skeletons, and
X represents a halogen atom or its salt, which comprises reacting an N-protected-α-amino acid ester represented by formula (1)

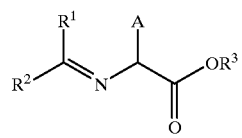

(1)

wherein
R¹ and R², independently from each other, represent an optionally substituted aryl group or lower alkyl group, or a hydrogen atom,
R³ represents an optionally substituted lower alkyl group, aralkyl group or aryl group, and
A is as defined above,
provided R¹ and R² may together form a ring structure with a halomethyllithium, and then treating this with an acid.

2. The process as claimed in claim 1, wherein X is a chlorine atom or a bromine atom.

3. The process as claimed in claim 1, wherein A is a benzyl group or a phenylthiomethyl group.

4. The process as claimed in claim 1, wherein both of R¹ and R² are optionally substituted aryl groups, or one of R¹ and R² is an optionally substituted aryl group and the other is a hydrogen atom.

5. The process as claimed in claim 1, wherein R³ is an optionally substituted lower alkyl group or aralkyl group, X is a halogen atom, and the halomethyllithium is formed with a lower alkyllithium and a dihalomethane.

6. A process for producing an α-aminohalomethylketone represented by formula (3)

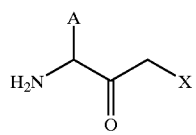

(3)

wherein
A represents an optionally substituted alkyl group having 1 to 10 carbon atoms, an optionally substituted aryl group having 6 to 15 carbon atoms, an optionally substituted aralkyl group having 7 to 20 carbon atoms, or a group in which heteroatom is contained in these carbon skeletons, and
X represents a halogen atom or its salt, which comprises reacting an N-protected-α-amino acid ester represented by formula (1)

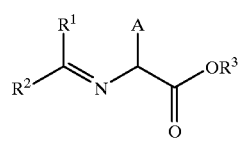

(1)

wherein
R¹ and R², independently from each other, represent an optionally substituted aryl group or lower alkyl group, or a hydrogen atom,
R³ represents an optionally substituted lower alkyl group, aralkyl group or aryl group, and
A is as defined above,
provided R¹ and R² may together form a ring structure, with a halomethyllithium to form an N-protected-α-aminohalomethylketone represented by formula (2)

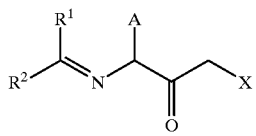

(2)

wherein $R^1$, $R^2$, A and X are as defined above, and treating this with an acid.

7. The process as claimed in claim 6, wherein $R^3$ is an optionally substituted lower alkyl group or aralkyl group, X is a halogen atom, and the halomethyllithium is formed with a lower alkyllithium and a dihalomethane.

8. A process for producing an N-protected-α-aminohalomethylketone represented by formula (2)

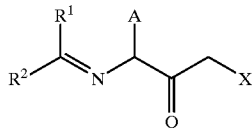

(2)

wherein
$R^1$ and $R^2$, independently from each other, represent an optionally substituted aryl group or lower alkyl group, or a hydrogen atom, A represents an optionally substituted alkyl group having 1 to 10 carbon atoms, an optionally substituted aryl group having 6 to 15 carbon atoms, an optionally substituted aralkyl group having 7 to 20 carbon atoms, or a group in which heteroatom is contained in these carbon skeletons, and X represents a halogen atom, provided $R^1$ and $R^2$ may together form a ring structure, which comprises reacting an N-protected-α-amino acid ester represented by formula (1)

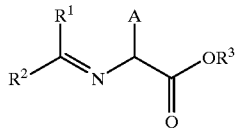

(1)

wherein
$R^1$, $R^2$ and A are as defined above, and
$R^3$ represents an optionally substituted lower alkyl group, aralkyl group or aryl group with a halomethyllithium.

9. The process as claimed in claim 8, wherein $R^3$ is an optionally substituted lower alkyl group or aralkyl group, X is a halogen atom, and the halomethyllithium is formed with a lower alkyllithium and a dihalomethane.

10. A process for producing an α-aminohalomethylketone represented by formula (3)

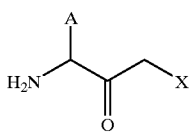

(3)

wherein
A represents an optionally substituted alkyl group having 1 to 10 carbon atoms, an optionally substituted aryl group having 6 to 15 carbon atoms, an optionally substituted aralkyl group having 7 to 20 carbon atoms, or a group in which heteroatom is contained in these carbon skeletons, and X represents a halogen atom or its salt, which comprises treating an N-protected-α-aminohalomethylketone represented by formula (2)

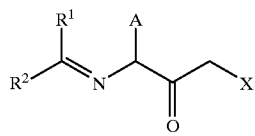

(2)

wherein
$R^1$ and $R^2$, independently from each other, represent an optionally substituted aryl group or lower alkyl group, or a hydrogen atom, and A and X are as defined above, provided $R^1$ and $R^2$ may together form a ring structure with an acid.

11. A process for producing an N-protected-α-aminohalomethylketone represented by formula (7)

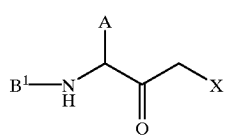

(7)

wherein
A represents an optionally substituted alkyl group having 1 to 10 carbon atoms, an optionally substituted aryl group having 6 to 15 carbon atoms, an optionally substituted aralkyl group having 7 to 20 carbon atoms, or a group in which heteroatom is contained in these carbon skeletons, X represents a halogen atom, and $B^1$ represents a protecting group of an amino group, which comprises obtaining the α-aminohalomethylketone represented by formula (3) or its salt by the process as claimed in claim 1, and then protecting the amino group with a protecting group.

12. An N-protected-α-aminohalomethylketone represented by formula (2)

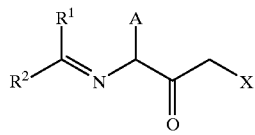

(2)

wherein
$R^1$ and $R^2$, independently from each other, represent an optionally substituted aryl group or lower alkyl group, or a hydrogen atom, A represents an optionally substituted alkyl group having 1 to 10 carbon atoms, an optionally substituted aryl group having 6 to 15 carbon atoms, an optionally substituted aralkyl group having 7 to 20 carbon atoms, or a group in which heteroatom is contained in these carbon skeletons, and X represents a halogen atom, provided $R^1$ and $R^2$ may together form a ring structure.

* * * * *